(12) United States Patent
Tieri et al.

(10) Patent No.: US 7,524,995 B1
(45) Date of Patent: Apr. 28, 2009

(54) CONTINUOUS PROCESS TO PRODUCE HEXAFLUOROISOPROPANOL

(75) Inventors: Stephen M. Tieri, Wilmington, DE (US); John Joseph Hagedorn, Newark, DE (US); James Arnold Schultz, Swedesboro, NJ (US); Tiberiu M. Leib, Voorhees, NJ (US); Susanne Hawthorne Wolff, Wilmington, DE (US); Sourav K. Sengupta, Wilmington, DE (US); Gregory Paul Shankwitz, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/138,002

(22) Filed: Jun. 12, 2008

(51) Int. Cl.
C07C 29/145 (2006.01)
(52) U.S. Cl. .................................................. 568/842
(58) Field of Classification Search .................. 568/842
See application file for complete search history.

(56) References Cited

U.S. PATENT DOCUMENTS

| | | | |
|---|---|---|---|
| 4,564,716 A * | 1/1986 | Katsuhara et al. | 568/842 |
| 6,005,143 A | 12/1999 | Machado et al. | |
| 6,123,835 A | 9/2000 | Ackerson et al. | |
| 6,428,686 B1 | 8/2002 | Ackerson et al. | |
| 6,506,361 B1 | 1/2003 | Machado et al. | |
| 6,610,628 B2 | 8/2003 | Nordquist et al. | |
| 6,881,326 B2 | 4/2005 | Ackerson et al. | |
| 7,291,257 B2 | 11/2007 | Ackerson et al. | |

FOREIGN PATENT DOCUMENTS

| | | |
|---|---|---|
| CN | 1962589 | 5/2007 |
| GB | 2 073 181 A | 10/1981 |
| JP | 58088330 | 5/1983 |
| JP | 59204142 | 11/1984 |
| JP | 01301631 | 12/1989 |
| JP | 1994184025 A | 7/1994 |
| JP | 202275107 A | 9/2002 |
| JP | 2003089666 A | 3/2003 |
| WO | WO 98/30323 | 7/1998 |
| WO | WO 02/26679 A1 | 4/2002 |
| WO | WO 2005/077873 A1 | 8/2005 |

OTHER PUBLICATIONS

Engelhard Material Safety Data Sheet, Ni-3288 E 1/16 3F Nickel Catalyst, MSDS Code: 0474128, Feb. 2, 2004.
Engelhard Information Sheet, Nickel Catalyst Ni-3288 E 1/16" 3F, no date.
Johnson Matthey Catalysts Safety Data Sheet, Nickel/nickel oxide catalyst, Revision 04-UK00, May 2004; Johnson Matthey Chemicals GmbH, Germany.
Machado et al., Applying monolith reactors for hydrogenations in the production of specialty chemicals - process and economic considerations; Catalysis Today (2005), 105, 305-317; Elsevier B.V.

* cited by examiner

Primary Examiner—Elvis O Price
(74) Attorney, Agent, or Firm—Kathryn M. Sanchez

(57) ABSTRACT

A continuous process for producing hexafluoroisopropanol is provided which comprises contacting hexafluoroacetone with hexafluoroisopropanol and hydrogen to produce a liquid feed stream; introducing the liquid feed stream to a reactor containing an immobilized hydrogenation catalyst to convert the hexafluoroacetone to hexafluoroisopropanol and provide a product stream; and recovering at least a portion of the hexafluoroisopropanol from the product stream. Preferably a portion of the product stream is recycled. The reactor can be a packed bed or stirred tank reactor.

24 Claims, 1 Drawing Sheet

CONTINUOUS PROCESS TO PRODUCE HEXAFLUOROISOPROPANOL

BACKGROUND OF THE INVENTION

Hexafluoroisopropanol (1,1,1,3,3,3-hexafluoro-2-propanol, abbreviated herein as HFIP) is used as an intermediate for pharmaceuticals and agrochemicals, as a solvent or cleaner in electronics, and in analytical applications due to its ability to dissolve a variety of polymers. HFIP exhibits strong hydrogen bonding and will associate with and dissolve most molecules with receptive sites such as oxygen, double bonds, or amine groups. Stable distillable complexes are formed with many ethers and amines due to strong hydrogen bonding. HFIP is soluble in water and most organic solvents. It is a volatile (b.p. 58.2° C.) and polar material, with high density, low viscosity, and low surface tension. HFIP is transparent to UV light and has a low refractive index.

Typically, hexafluoroisopropanol (HFIP) is prepared by the hydrogenation of hexafluoroacetone (HFA) and/or HFA hydrate, for instance using a batch reactor containing a slurry catalyst. Such processes have limited capacity and relatively long cycle times; while catalyst attrition, removal of catalyst fines, and catalyst recovery are problematic.

Katsuhara et al. in U.S. Pat. No. 4,564,716 describe a process for the hydrogenation of HFA hydrate using a heterogeneous catalyst system that is typical of batch hydrogenation processes. Katsuhara et al. disclose HFA hydrate is hydrogenated rather than HFA, to reduce concerns with reacting high concentrations of toxic HFA and the pressures that would be required to contain the low boiling HFA (−28° C.) at reaction temperatures (700-100° C.). In this process the catalyst settles in the reactor at the end of a batch. A portion of the liquid product is then drawn off, but about 10% of the catalyst is drawn off with the liquid, requiring added catalyst to make-up the initial charge, and complicating catalyst recovery.

Batch hydrogenation has deficiencies compared with continuous processes, for instance the energy and cycle time that are required to heat up and cool down each batch. As a result, the reaction time in a batch process is only a fraction of the overall cycle time, and therefore the productivity of the reactor is much lower than for a continuous system.

Kawai et al., in GB 2,073,181, describe a process for the continuous vapor phase hydrogenation of HFA to form HFIP by passing a mixture of HFA and hydrogen across a fixed bed of solid catalyst at 300-140° C. While an improvement over a batch process, vapor phase hydrogenation processes also have disadvantages. There is a high temperature rise across the catalyst bed due to the heat released from the exothermic hydrogenation reaction. This temperature rise can cause catalyst bed hot spots, which can result in byproduct formation, including the formation of hydrofluoric acid, and reduced catalyst life.

Demand for HFIP in the applications listed above is increasing rapidly. It is desirable to improve available processes for the hydrogenation of HFA. The present invention provides such a process.

SUMMARY OF THE INVENTION

The present invention provides a continuous process for producing hexafluoroisopropanol which comprises: (a) contacting hexafluoroacetone with hexafluoroisopropanol and hydrogen in a mixing device to produce a liquid feed stream; (b) introducing the liquid feed stream to a reactor containing an immobilized hydrogenation catalyst to convert the hexafluoroacetone to hexafluoroisopropanol and provide a product stream; and (c) recovering at least a portion of the hexafluoroisopropanol from the product stream. This process applies to steady-state operation, in contrast to start-up. That is, during start-up, the reactor system, which comprises the mixing device and reactor are filled and no hexafluoroisopropanol is recovered.

The reactor can be a packed bed or slurry reactor. Preferably the reactor is a packed bed reactor. Advantageously, at least a portion of the product stream is recycled by recirculating to the mixing device to supply HFIP in step (a).

DETAILED DESCRIPTION

Figure 1:
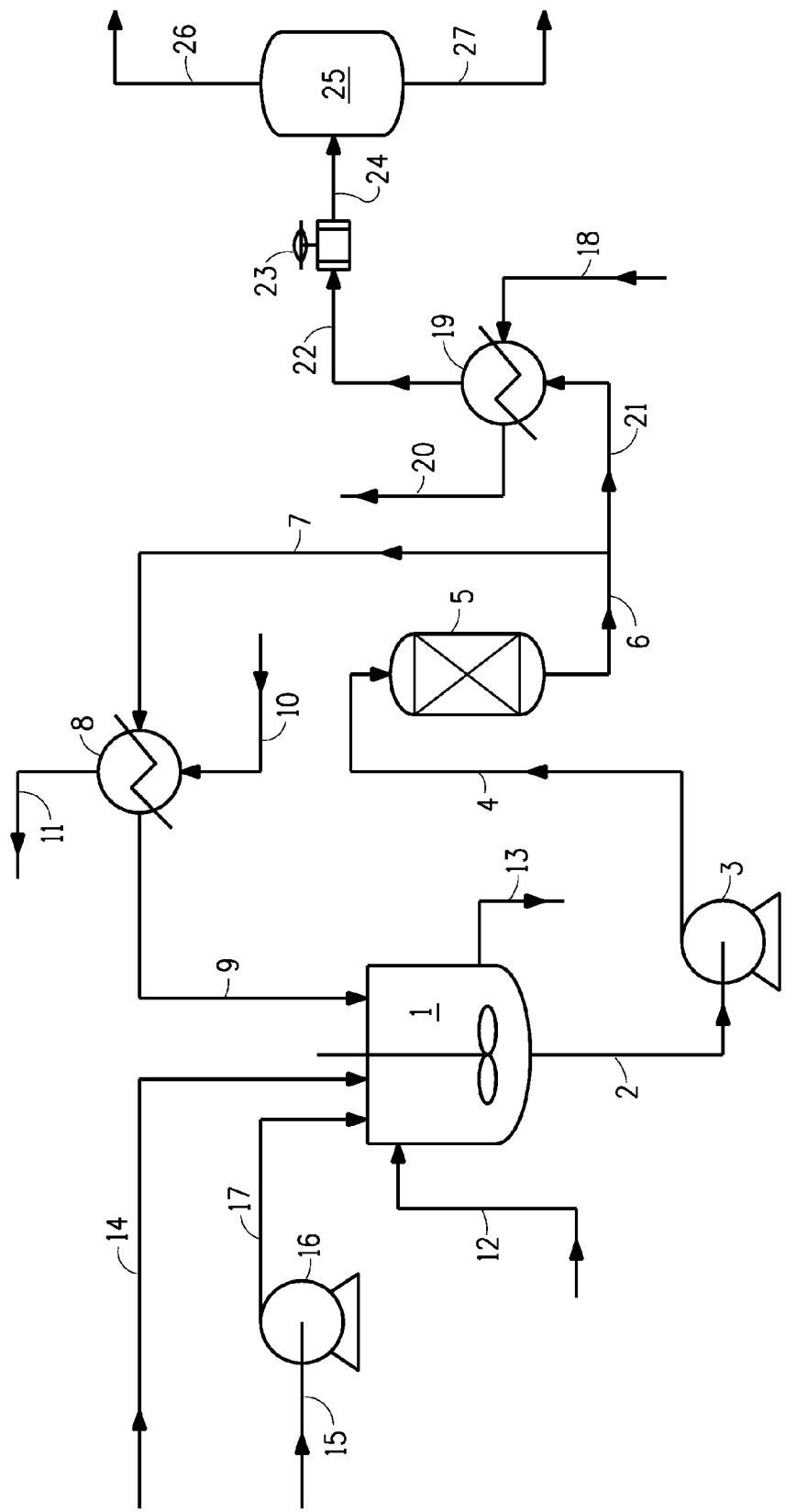
FIG. 1 is a flow diagram of a continuous reactor system with a packed bed reactor useful in this invention.

The present invention comprises a continuous liquid phase process for producing hexafluoroisopropanol (HFIP) in a reactor system which comprises a mixing device and a reactor. The process comprises (a) contacting hexafluoroacetone (HFA) with hexafluoroisopropanol (HFIP) and hydrogen in a mixing device to produce a liquid feed stream; (b) introducing the feed stream to a reactor containing an immobilized hydrogenation catalyst to convert the HFA to HFIP to provide a hydrogenated product stream, and (c) recovering at least a portion of the HFIP from the product stream. Preferably at least a portion of the product stream is recycled by recirculating to the mixing device to supply HFIP in step (a).

Contacting Step for HFA/HFIP and Hydrogen

The first step in the process of this invention is contacting HFA with HFIP and hydrogen in a mixing device to produce a liquid feed stream. The HFA may be contacted with HFIP and hydrogen sequentially, in either order or simultaneously. HFIP may be added as a solvent or HFIP may be added as a portion of the hydrogenated product stream, that is, as a recycle stream. The temperature, pressure and relative amounts of HFA and HFIP in this contacting step are set such that HFA is dissolved in HFIP and the mixture is a solution of HFA in HFIP.

The feed stream is substantially in the liquid form. It is preferred that the hydrogen is dissolved in the liquid HFA/HFIP solution; however, the liquid stream may comprise some hydrogen in the gas phase. Preferably, hydrogen is added in an amount and at a rate to saturate the HFA/HFIP solution.

The contacting step may occurs in a mixing device. By "mixing device" is meant in broad terms any system in which contacting the HFA with HFIP and hydrogen occurs in a manner so as to create a mixing effect. For example, the mixing device can be at an intersection of feed lines for HFIP and HFA and hydrogen. More typically the mixing device is a mixing vessel. Preferably the mixing device is selected from the group consisting of a mechanically agitated tank, such as an autoclave, or an in-line static mixer.

In a preferred process, HFA, HFIP, and hydrogen are fed continuously and simultaneously to an autoclave, which is a mixing tank, to produce a liquid feed stream comprising HFA, HFIP and hydrogen. HFA is fed using a piston pump. Hydrogen is fed and pressure is maintained at 300-2000 pounds/inch$^2$ gauge (hereinafter "psig", 2.17-13.9 MPa), preferably 400-1500 psig (2.86-10.4 MPa), and more preferably 600-1000 psig (4.24-7.00 MPa). Hydrogen pressure is measured and maintained within a desired pressure range in the headspace of the mixing device. Agitation provides adequate mixing sufficient to prevent mass transfer limitations and keep the liquid HFIP in the tank essentially saturated with hydrogen. The feed stream produced in the contacting step comprises HFIP, HFA and hydrogen.

Hydrogen gas bubbles may form during the contacting step (a) and be present in the feed stream. When such bubbles form, the process of this invention preferably further comprises a step of dis-engaging hydrogen gas bubbles that form during the contacting step (a) from the feed stream before introducing the stream to the reactor in step (b), thus preventing excess hydrogen entrainment to the reactor, which may otherwise cause reduced efficiency and reduced per pass conversion.

At start-up, in contrast to steady state, the stream comprises up to 100% HFIP. All percents are provided as mole %, unless otherwise noted. At start-up, the stream comprises close to 0% HFA. It is recognized that the system may be charged with 100% HFIP and slowly build to a desired concentration of HFA for steady-state operation. The process of this invention thus may comprise prior to step (a), a start-up procedure which comprises feeding HFIP sequentially to a mixing device and a reactor, and recirculating the HFIP from the reactor to the mixing device. During this process, heat is applied to the mixing device to heat the HFIP.

During steady-state operation, the feed stream comprises 70 to close to 100%, preferably 85 to 98%, HFIP, and more preferably 93-97% HFIP. During steady-state, the feed stream comprises from close to 0% to 30%, preferably 2-15%, HFA, and more preferably 3-7% HFA.

Hydrogen, including dissolved hydrogen, that is, hydrogen dissolved in the liquid feed stream comprising HFA and HFIP is present in an amount of 0-10%, and preferably 2-6%. Solubility depends on pressure.

The contacting step is performed at a temperature to provide a feed stream having a temperature of 75-160° C., preferably to 100-150° C. and more preferably to 120-140° C. In preferred process, temperature of the feed stream is maintained during continuous operation at a set or selected temperature by removing heat in a cooler from the hydrogenated product stream and recirculating the cooled product stream to the contacting step.

HFIP is both a solvent and a product from hydrogenation of HFA. Higher concentration of HFIP in the feed stream improves ability to moderate temperature in the system due to the exothermic hydrogenation reaction and substantially reduces the vapor pressure of HFA.

The feed stream comprising HFA, HFIP, and hydrogen can be fed to a catalytic packed bed reactor at a rate of 10 to 320 kg/min./ft$^2$ (108 to 3440 kg/min./m$^2$) based on catalyst bed cross sectional area; preferably 50-250 kg/min./ft$^2$ (538 to 2690 kg/min./m$^2$), most preferably 130-200 kg/min./ft$^2$ (1400 to 2150 kg/min./m$^2$).

Hydrogenation

The hydrogenation step (b) can be performed in one or more reactors. When more than one reactor is used, the reactors may be arranged in series, in parallel, or in both parallel and series. The reactor can be a packed bed or slurry reactor.

Preferably, the reactor is a packed bed reactor. An advantage of a packed bed reactor, which is a fixed bed reactor, is that the separation of reactants and products from the catalyst is simple.

The hydrogenation step may also be performed in one or more continuous stirred tank reactors where the catalyst is present in a slurry during the hydrogenation step. When using a stirred tank reactor, the catalyst may be held in a basket to avoid an additional process step of separating catalyst from the liquid product stream.

The liquid feed stream comprising HFA, HFIP and dissolved hydrogen is introduced to one or more reactors where hydrogenation of HFA occurs to produce HFIP in the product stream.

When using one or more packed bed reactors, the reactors can be up-flow or down-flow configurations. Performing the hydrogenation step in an up-flow configuration has the advantage of minimizing potential for hydrogen gas accumulation in the bed which may reduce the effective wetted catalyst surface area and reaction conversion per pass. Performing the hydrogenation step in a down-flow configuration minimizes potential for bed fluidization and catalyst fines entrainment. When hydrogen gas bubbles form during the contacting step and when operating in a down-flow configuration, the process preferably further comprises disengaging hydrogen gas bubbles in a gas/liquid disengagement device at the inlet of the reactor.

The temperature of the liquid feed to the catalyst bed and of the catalyst bed significantly impacts HFA conversion. Higher conversions occur at higher temperatures. The catalyst bed temperature is from 75° to 160° C. and preferably from 120° to 150° C. Lower temperatures lower conversion while higher temperatures generate excessive pressures and have the potential to reduce catalyst life or produce acid fluoride byproducts.

The operating pressure in the reactor is substantially the same as the pressure in the mixing device.

The product stream comprises HFIP and may further comprise unreacted hydrogen and/or unreacted HFA. During steady-state operation, a portion of this product stream may be drawn off as a side stream from the product stream, for example through a "T" or a splitter, and recirculated to the contacting step. This portion may provide all or a part of the HFIP present in the feed stream.

For adiabatic reactor configurations, at greater recirculation rates the temperature rise across the catalyst bed is lower, and conversely at lower recirculation rates, the temperature rise across the catalyst bed is higher.

The hydrogenation step of the present invention comprises contacting the liquid HFA/HFIP/hydrogen feed stream produced in contacting step (a) with a hydrogenation catalyst. In this step, HFIP acts as solvent or diluent in the feed mixture. The feed stream is then contacted with the hydrogenation catalyst.

The hydrogenation step of this invention is preferably performed in a packed bed reactor, such as plug flow, tubular or other fixed bed reactor packed with catalyst for feed and hydrogen to react. It should be understood that the packed bed reactor may be a single packed bed or multiple beds in series or in parallel or in a combination thereof as discussed hereinabove. No additional hydrogen is required; therefore trickle bed operation is avoided.

In the hydrogenation step, the feed stream (HFA/HFIP/hydrogen mixture) is a substantially hydrogen-gas-free liquid feed stream. The feed stream can be produced by contacting HFA with hydrogen and HFIP to produce a hydrogen-saturated liquid feed. Alternatively or in addition, after contacting HFA with hydrogen and HFIP, hydrogen gas can be removed from the feed stream, for example, by known gas/liquid separation methods in a disengagement step. Processes for producing hydrogen-gas-free liquid feed streams are known, such as those disclosed in U.S. Pat. Nos. 6,123,835; 6,428,686; 6,881,326 and 7,291,257.

The percentage of hydrogen soluble in HFIP solvent/diluent is greater than the percentage of hydrogen soluble in the HFA reactant. Preferably all of the hydrogen required for reaction is made available in solution upstream of the packed bed reactor, thus eliminating the need to circulate hydrogen gas within the reactor.

The hydrogenation reaction is highly exothermic and as a result a great deal of heat is generated in the reactor. The temperature of the reactor can be controlled by using a recycle stream. A portion of the reactor effluent can be recycled back to the front of the reactor and blended with fresh feed and hydrogen. The process can be a multi-stage process using a series of two or more reactors in series and fresh hydrogen can be added at the inlet of each reactor. The recycle stream absorbs some of the heat and reduces the temperature rise through the reactor. The reactor temperature can be controlled by controlling the fresh feed temperature and the amount of recycle. In addition, because the recycle stream comprises reacted components, such as HFIP, the recycle stream also serves as an inert diluent. Optionally, a finishing reactor can be used, for example to hydrogenate small quantities of HFA remaining.

Catalyst

Each reactor contains therein an immobilized hydrogenation catalyst. "Immobilized catalyst" is defined herein as a stationary catalyst that is retained within the reactor, as in a bed or a basket or otherwise fixed in place within the reactor and does not need to be separated from the liquid product stream as a separate process step. The catalyst is a formed catalyst particle comprising a catalytic metal or mixture of catalytic metals. The catalytic metal may be dispersed on a support such as a metal oxide, a mixed metal oxide, or carbon. For clarity, the term metal oxide includes silica. Monolith catalysts are also contemplated herein (see, for example, U.S. Pat. No. 6,506,361).

The catalytic metal has hydrogenating activity ("active metal"), and is selected from the group consisting of metal in Groups IB, VIIB, VIIB and VII of the Periodic Table. Preferably, the catalyst comprises at least one metal selected from the group consisting of chromium, molybdenum, tungsten, iron, cobalt, nickel, copper, ruthenium, rhodium, palladium, osmium, iridium and platinum. More preferably, the catalyst comprises nickel. The metal may be in the zero valent oxidation state or in the form of a compound, such as an oxide. The metal may be supported or not supported. The metal may be a Raney-type.

Optionally, a metal promoter may be used with the catalytic metal in the method of the present invention. Suitable metal promoters include tin, copper, silver, and gold. These promoters can be used in combination with Group VII metals of the Periodic Table. Promoters are typically used in amounts less than about 10% by weight of the catalytic metal.

The support is a porous solid with high total surface areas (external and internal) which can provide high concentrations of active sites per unit weight of catalyst. Preferably the support has pores of a relatively small diameter that is preferably 50 nm or less. Preferred supports have a surface area greater than 20 m$^2$/g, more preferably, the support has a surface area greater than 75 m$^2$/g, still more preferably the support has a surface area of at least 100 m$^2$/g. The catalyst support may enhance the function of the catalytic metal. Supported catalysts are generally preferred because the catalytic metal is used more efficiently. Generally surface area is less than 300 m$^2$/g.

Suitable supports include metal oxides, mixed metal oxides and carbons. Oxide supports include alumina, silica, silica-alumina, zeolite, kieselguhr, titania, titania-alumina, titania-silica, zirconia, lanthanum oxide, magnesium oxide, barium oxide, calcium oxide, zinc oxide, calcium carbonate, aluminum silicate, calcium silicate, and barium sulfate. Carbons include activated charcoal, graphite, and fibril nanotube carbon. A combination of supports may be used. Preferably the support is selected from the group consisting of alumina, silica, zirconia, activated charcoal, calcium silicate, graphite, and kieselguhr. More preferably the support is selected from the group consisting of alumina, silica, zirconia, calcium silicate, and kieselguhr.

Relative proportions of catalytic metal and support, while not critical, are important. If too little catalytic metal is present, initial activity will be lower than desired and a long activation period may be required for the catalyst to reach maximum activity. It will be appreciated that the higher the weight percent of metal, the faster the reaction. A preferred content range of the catalytic metal in a supported catalyst is from about 0.1 wt % to about 90 wt % based on the total weight of the supported catalyst. Preferably, the concentration of catalytic metal is from about 0.2 wt % to about 75 wt %. More preferably, the concentration of catalytic metal is from about 0.5 wt % to about 60 wt %.

In particular, when the catalytic metal or its oxide interacts with the support structure, for example, by forming a spinel phase, higher concentrations of catalytic metal are necessary. By higher concentration is meant the catalytic metal content is preferably 45 to 60 wt %, based on the total weight of the supported catalyst. For non-interactive supports, the metal concentration is lower, preferably 0.5 to 10 wt % of catalytic metal based on the total weight of the supported catalyst. Interactive supports include alumina and silica for certain catalytic metals including nickel and cobalt. Non-interactive supports include alumina for palladium and platinum, and zirconia for nickel and cobalt. Persons skilled in the art will recognize which supports interact with which metals and select catalytic metal/support compositions accordingly.

The catalyst is in the form of particles, preferably shaped particles. By "shaped particle" it is meant the catalyst is in the form of an extrudate. Extrudates include cylinders, pellets, or spheres. Cylinder shapes may have hollow interiors with one or more reinforcing ribs. Trilobe, cloverleaf, rectangular- and triangular-shaped tubes, cross, and "C"-shaped catalysts can be used.

Preferably the catalyst particle is about 0.01 to about 0.5 inch (about 0.25 to about 13 mm) in diameter when a packed bed reactor is used. More preferably, the catalyst particle is about 1/32 to about 1/4 inch (about 0.79 to about 6.4 mm) in diameter.

Catalysts are commercially available from numerous vendors. Alternatively catalysts can be prepared by a variety of ways known in the art. Various catalysts may be used, for instance Engelhard 1/16 inch (1.6 mm) 3F Ni-3288 E trilobe (Ni/mixed oxide support), or other nickel catalysts on inert supports such as nickel on kieselguhr or nickel on alumina catalysts. Other catalysts and catalyst particle shapes may be used, such as Johnson Matthey HTC Ni500RP trilobe catalyst (Ni/alumina). The metal catalysts suitable for the process of the present invention are indicated above on a high surface area inert support that is stable in the process environment may be substituted.

A wide range of suitable catalyst concentrations may be used. The amount of catalyst per reactor is generally dependent on the reactor type. For a packed bed reactor, the volume of catalyst per reactor will be high, while in a slurry, the volume will be lower. Typically, in a slurry reactor, the catalyst will make up 0.1 to about 30 wt % of the reactor contents. Preferably, the catalyst is 1 to 15 wt % of the reactor contents.

Catalyst Regeneration

Deactivation of a catalyst is an integral part of a catalyst lifecycle. Therefore, catalyst regeneration plays an important role in the economics of the overall process. In the present invention, advantageously the catalyst can be regenerated after the catalyst deactivates to a certain level, i.e., the conversion of HFA and/or selectivity of HFIP drops below a pre-defined value. The catalyst can be regenerated and its activity and selectivity can be restored to substantially its original value.

A regeneration process of the catalyst comprises treating the catalyst in the presence of hydrogen at elevated temperature and pressure, optionally treating the catalyst in the presence of an oxygen-containing gas at elevated temperature, followed by hydrogen treatment at elevated temperature and pressure.

Recovery Process Step

The product stream is continuously removed from the reactor during steady state operation. At steady state, HFA addition rate can be matched with product stream removal (take-off) rate. The HFA addition rate and product stream removal rate provide flow for recirculaton.

HFIP is recovered from the product stream, which comprises HFIP, using conventional methods. This stream may further comprise unreacted hydrogen and/or unreacted HFA. The product stream is cooled and pressure in the stream is reduced for subsequent purification. The recovery step thus comprises cooling the product stream and reducing pressure of the product stream. The cooled, de-pressurized stream is then fed to a gas/liquid separator in which hydrogen and small amounts of HFA and/or HFIP in the vapor phase are separated from a liquid stream comprising HFIP. Further purification may be by distillation or other purification methods known to those skilled in the art.

Compared with the process described by Katsuhara in U.S. Pat. No. 4,564,716, after initial startup, the continuous process of the present invention is always at operating temperature and has the advantage of an immobilized catalyst. Using an immobilized catalyst eliminates the need for routine catalyst handling, filtration equipment, and requires smaller volume reaction equipment because of the greater overall reactor productivity. The recirculating liquid HFIP stream through the reactor system results in high mass transfer rates to the catalyst surface, which minimizes amount of catalyst needed, and prevents the formation of hot spots in a packed bed, which improves catalyst life. Because the HFA concentration in the reactor can be 2% or less, HFA can be hydrogenated directly eliminating the need to make HFA hydrate from HFA. At such low concentrations HFA is more easily and safely handled due to its toxicity and low boiling point. In a batch reactor the initial HFA concentration is much greater. The lower HFA concentration in the process of the present invention (more than an order of magnitude less) reduces safety, health and environmental hazards of HFA.

Compared with the process described by Kawai et al., in GB 2,073,181, the recirculating liquid phase process of the present invention has advantages. The relatively low temperature increase across the reactor allows excellent temperature control in the hydrogenation step, minimizing byproduct formation, including hydrofluoric acid formation, and leads to improved catalyst life.

Process Description Based on FIG. 1

The process of the present invention can be affected, for example in the equipment illustrated in FIG. 1. Those skilled in the art will recognize that many components are readily changed from those specifically illustrated in FIG. 1. Thus FIG. 1 is not intended to limit the liquid phase catalyzed hydrogenation process of the present invention. The key items of the process comprise a recirculating hydrogenation system comprising a mixing device, a reactor, a recirculation loop, and a product stream take-off to a gas/liquid separator. At start-up, the system is filled with HFIP.

The general operation of the process of the present invention for the system illustrated in FIG. 1 is now described. FIG. 1 is a simplified schematic diagram of a reactor system suitable for use for the process of this invention. A mixing device 1 may consist of a mechanically agitated tank, a jet of flowing liquid impinging on a liquid surface, or piping tees on either side of one or more static mixing devices. As illustrated mixing device 1 is an autoclave. Mixing device 1 contains a liquid comprising hydrogen, HFIP and HFA. A liquid stream 2 comprising HFIP and HFA that is saturated with hydrogen is fed to transfer device 3, which is shown as a pump. The liquid in mixing device 1 is saturated with hydrogen by providing sufficient mass transfer in mixing device 1 to prevent hydrogen mass transfer limitations. Mixing device 1 also provides for disengaging hydrogen bubbles from stream 2 to minimize gas entrainment to transfer device 3 or packed bed reactor 5.

Transfer device 3 feeds liquid stream 4 to packed bed reactor 5, which contains catalyst particles (not shown). Liquid stream 4 comprises hydrogen, HFA and HFIP. HFIP is produced in packed bed reactor 5 through the exothermic hydrogenation of HFA. Although packed bed reactor 5 is illustrated as a single reactor, multiple packed beds in series, in parallel, or in both series and parallel may be used. Optionally, when multiple reactors are used, the reactor system may comprise intermediate hydrogen feed systems and intermediate mixing devices between the individual packed beds. Each packed bed may be constructed from either piping packed with catalyst particles, which would result in adiabatic operation, or from a heat transfer device, such as a shell and tube heat exchanger with the catalyst contained within the tubes, to allow near isothermal operation.

Product stream 6 exits packed bed reactor 5. A recirculation loop is created by diverting a portion of product stream 6 as side stream 7 for return to mixing device 1. The portion of the stream 6 representing the fraction of stream 6 to be recycled as stream 7 can be anywhere from 0 to 1, that is none of stream 6 is diverted or all of stream 6 is diverted as stream 7, depending on the configuration of packed bed reactor 5 and the desired HFIP production rate.

Recirculation cooler 8 may be used to remove heat of reaction, if desired, from side stream 7. Coolant supply stream 10 is fed to recirculation cooler 8 to remove heat from side stream 7. Coolant exits recirculation cooler 8 as coolant return stream 11 and coolant may be recycled through a heat exchanger or other suitable device (not shown). After side stream 7 is cooled, it becomes cooled recycle stream 9, which exits recirculation cooler 8 and flows back to mixing device 1.

Heating fluid is fed to mixing device 1 as heating media supply stream 12, for heating contents of mixing device 1. Heating fluid exits mixing device 1 as heating media return stream 13 and heating fluid may be recycled through a heat exchanger or other suitable device (not shown). It is recognized that alternatives, such as electricity may be used to supply heat to mixing device 1 rather than a heating fluid as illustrated. The temperature of the liquid in mixing device 1 is controlled at a reaction temperature set point by adjusting flow of heating fluid in heating media supply stream 12 and heating media return stream 13 to mixing device 1 or by adjusting flow of coolant in coolant supply stream 10 and coolant return stream 11 to recirculation cooler 8.

Hydrogen is fed to mixing device 1 as hydrogen-containing gas stream 14 as needed to maintain the system pressure at the desired set point. HFA is fed as liquid HFA stream 15 to transfer device 16, which can be, for example, one or more metering pumps. Liquid HFA stream 17 from transfer device 16 is fed to mixing device 1 to obtain the desired HFIP production rate.

Product stream 21, after removing side stream 7 from product stream 6 is fed to product stream cooler 19. Product stream cooler 19 may be used to reduce product temperature and minimize HFIP losses from the process when pressure is reduced. Coolant supply stream 18 is fed to product stream cooler 19 to remove heat from product stream 21. Coolant exits product stream cooler 19 as coolant return stream 20 and coolant may be recycled through a heat exchanger or other suitable device (not shown).

Product stream 21 may be fed to a finishing reactor (not shown in FIG. 1) upstream of product cooler 19 to further reduce HFA present in product stream 21 and thus HFA concentration in the final HFIP product.

Product stream 21 is cooled in product stream cooler 19 and becomes cooled product stream 22. Cooled product stream 22 is fed to pressure reducing device 23. Pressure reducing device 23 can be any suitable pressure reducing device, such as a control valve. Pressure reducing device 23 reduces pressure of cooled product stream 22 to provide product stream 24. The flow rate of product stream 24 can be adjusted using pressure reducing device 23 to maintain a liquid level in mixing device 1 at a set point. Product stream 24 exiting pressure reducing device 23 is fed to gas/liquid separator 25, which provides gas stream 26 and liquid HFIP product stream 27. Gas stream 26 comprises primarily hydrogen, with trace amounts of HFA and HFIP. Gas stream 26 is sent to a scrubber. Liquid HFIP product stream 27 exits gas/liquid separator 25 and is collected for further purification.

Materials and Test Methods

Engelhard 1/16 inch (1.6 mm) 3F Ni-3288 E trilobe catalyst is a supported nickel catalyst in trilobe form obtained from Engelhard, DeMeem, Netherlands. The support is a mixture of metal oxides including bentonite clay and alumina.

Johnson Matthey HTC Ni500RP catalyst is a supported nickel/nickel oxide catalyst in trilobe form, obtained from Johnson Matthey Chemicals, Emmerich am Rhein, Germany. The support is alumina.

HFA and HFIP were obtained from E. I. du Pont de Nemours and Company, Wilmington, Del.

EXAMPLES

The procedures for start up and for continuous operation of the preferred process as used in the following Examples are described. The Examples provide the process variables used.

The Examples were performed in a reaction system similar to that of FIG. 1. The mixing device 1 was a 1-liter 316 stainless steel autoclave equipped with an agitator, means of heating, with a design pressure of 2000 psig (13.9 MPa). HFA was fed to the autoclave with an Isco syringe pump 16 Model 1000D. Pump 3 was a Lewa Ecoflow 319 stainless steel diaphragm pump with a design pressure of 1500 psig (10.4 MPa). The reactor 5 was a 16×1 inch (40.6×2.54 cm) 316 stainless steel Schedule 80 pipe. Product was collected in a 17×4 inch (43.2×10.2 cm) 304 stainless steel gas/liquid separator 25, with a capacity of 2.25 L. Catalysts used were Engelhard 1/16 inch (1.6 mm) 3F Ni-3288 E trilobe catalyst (41.5 g) and Johnson Matthey HTC NI500RP trilobe (39.2 g).

In the process of the Examples, liquid HFIP (1.4 kg) was charged to the autoclave 1. A liquid stream 2 comprising HFA, HFIP and hydrogen was fed using a pump 3 and a feed stream 4 to a packed bed reactor 5 that had been previously loaded with catalyst particles. The liquid product stream 6, exiting the reactor was divided into a side stream 7, which was fed back to the mixing device 1. Electric heat was supplied to mixing device 1 to heat the liquid contents and control the liquid temperature at the reaction temperature set point.

The liquid in the mixing device 1 was saturated with hydrogen by feeding a hydrogen supply stream 14 to the mixing device 1 as needed to maintain the mixing device 1 pressure at the desired set point. A liquid HFA feed stream 15 was fed through a transfer device 16 that controlled the rate of HFA feed rate 17 to the mixing device 1 at the desired flow rate.

A coolant supply stream 18 cooled the product stream 21 in the product cooler 19, and a coolant return stream 20 flowed from the product cooler 19. A product stream 21 comprising primarily HFIP and excess hydrogen was removed from the exit of the packed bed reactor 5 as needed to maintain the level in the mixing device 1 at set point. The product stream 22 passed through the product cooler 19 to reduce the stream temperature and minimize product losses from the process when the system pressure was reduced. The cooled product stream 22 was fed to a control valve pressure reducing device 23 before the lower pressure stream 24 exiting the control valve was sent to a gas/liquid separator 25. The gas stream 26 from the separator containing primarily excess hydrogen and trace amounts of HFA and HFIP was sent to a scrubbing system. Liquid HFIP product 27 was collected from the separator for further purification.

The packed bed up-flow reactor used in the Examples comprised a 1 inch (2.54 cm) outer diameter stainless steel tube with an inner diameter of 0.834 inch (2.12 cm) and an overall length of 10.5 inch (26.7 cm). A multi-element thermocouple was installed in the reactor for measurement of inlet and bed temperatures throughout the bed. The catalyst bed itself consisted of 6 inches (15.2 cm) of 1/16 inch (1.6 mm) Ni-32880E trilobe catalyst with a total weight of 41.5 g. Catalyst retention mesh screens were used directly on the top and bottom of the catalyst bed to hold the main catalyst particles in place. A 2 to 2.5-inch (5.09 to 6.35 cm) deep section of 1/8 inch (3.2 mm) stainless steel balls was placed above and below the mesh screens—to ensure a uniform flow pattern through the bed. Finally, 100-micrometer porous metal supports were installed at the bottom and at the top of the reactor adjacent to the feed inlet and product outlet to support the internals and retain fine catalyst particles within the reactor.

Example 2 used the same reactor configuration as described above, except the reactor was used in a down-flow configuration instead of an up-flow configuration. The reactor feed entered at the top of the bed and the product was withdrawn from the bottom of the bed.

Example 9 used essentially the same up-flow reactor configuration except 6 inches (15.2 cm) of Johnson Matthey HTC Ni500 1.2RP trilobe catalyst with a total weight of 39.16 g was used.

Example 1

1400 g of HFIP was charged to the mixing device. The agitation speed was set at 800 revolutions/min. (hereinafter "rpm"). 41.5 g of Engelhard 1/16 inch (1.6 mm) 3F Ni-3288 E trilobe catalyst was charged to the packed bed. As detailed in Table 1, conditions were as follows: HFA feed rate was 150 g/hr, and reaction temperature was 120° C., mixing device pressure was maintained at 600 psig (4.24 MPa) by controlling hydrogen addition, and recirculation flow rate was 100 mL/min. Circulation through the packed bed was in the up-flow configuration. The run conditions were held for 3 hours after steady state was reached. An 11° C.-temperature rise was observed across the packed bed from inlet to outlet. As summarized in Table 1, the total HFA molar conversion was 99.94% and the measured residual HFA concentration was 627 mg/kg (as measured by gas chromatography, "GC" area percent). The HFIP product purity (by GC area percent) and corresponding HFIP yield was 98.74%. The run results are summarized in Table 2.

Example 2

All conditions were the same as Example 1 except that the circulation through the packed bed was in the down-flow configuration. The run duration at steady state was 6 hours. A 9° C.-temperature rise was observed across the packed bed. The total HFA molar conversion was 99.93% with a residual HFA concentration of 699 mg/kg (by GC area percent). The run results are summarized in Table 2.

Examples 3-8

All conditions were the same as Example 1, except as shown in Table 1. The run results are summarized in Table 3.

Example 9

All conditions were the same as Example 1 except that the catalyst was 39.2 g of Johnson Matthey HTC Ni500RP trilobe catalyst (Ni/alumina). The run duration at steady state was 6.5 hours. A 7° C.-temperature rise was observed across the packed bed. The HFIP product purity (by GC area percent) was 99.61% with a residual HFA concentration of 14 mg/kg (by GC area percent). The total HFA molar conversion was greater than 99.99%. The run results are summarized in Table 3.

TABLE 1

Reactor Conditions

| Example | HFA Feed Rate, g/h | Reaction Temp., ° C. | Reactor Pressure, psig (MPa) | Recirculation Flow Rate, mL/min. |
|---|---|---|---|---|
| 1 | 150 | 120 | 600 (4.24) | 100 |
| 2* | 150 | 120 | 600 (4.24) | 100 |
| 3 | 150 | 120 | 900 (6.31) | 125 |
| 4 | 86 | 120 | 600 (4.24) | 100 |
| 5 | 180 | 120 | 900 (6.31) | 87 |
| 6 | 86 | 100 | 600 (4.24) | 100 |
| 7 | 180 | 130 | 600 (4.24) | 100 |
| 8 | 150 | 140 | 600 (4.24) | 100 |
| 9 | 150 | 120 | 600 (4.24) | 100 |

*Example 2 used down-flow configuration.

The agitation speed was set at 800 rpm for all Examples.

TABLE 2

Example Product Analyses

| Example | HFA*, wt. % | HFIP*, wt. % | Total Conversion, % | Run Duration, h | Temp. rise across bed, ° C. |
|---|---|---|---|---|---|
| 1 | 0.0627 | 98.74 | 99.94 | 3 | 11 |
| 2 | 0.0699 | 98.55 | 99.93 | 6 | 9 |
| 3 | 0.0507 | 98.36 | 99.94 | 2.5 | 8 |
| 4 | 0.0105 | 99.56 | 99.99 | 2 | 7 |
| 5 | 0.1081 | 98.29 | 99.89 | 3.5 | 15 |
| 6 | 0.4199 | 98.09 | 99.58 | 3.5 | 6 |
| 7 | 0.0414 | 98.92 | 99.96 | 3 | 13 |
| 8 | 0.0164 | 99.20 | 99.99 | 4 | 12 |
| 9 | 0.0014 | 99.61 | >99.99 | 6.5 | 7 |

*HFA and HFIP and other trace compounds ad centum.

Table 2 shows that a continuous reactor with HFIP recycle can achieve a high HFA conversion (>99.5%) with a high HFIP yield over a wide range of operating conditions. This performance can be obtained with both up-flow and down-flow operation and with different catalysts. HFIP recycle results in a low temperature rise across an adiabatic packed bed (<15° C.), even at the lowest recycle rates tested.

What is claimed is:

1. A continuous process for producing hexafluoroisopropanol comprising:
   (a) contacting hexafluoroacetone with hexafluoroisopropanol and hydrogen in a mixing device to produce a liquid feed stream;
   (b) introducing the liquid feed stream to a reactor containing an immobilized hydrogenation catalyst to convert the hexafluoroacetone to hexafluoroisopropanol and provide a product stream; and
   (c) recovering at least a portion of the hexafluoroisopropanol from the product stream.

2. The process of claim 1 wherein the reactor is a packed bed reactor.

3. The process of claim 1 further comprising recirculating at least a portion of the product stream produced in step (b) to step (a) as the source of hexafluoroisopropanol.

4. The process of claim 2, wherein step (b) is performed in two or more packed bed reactors.

5. The process of claim 1 further comprising, prior to step (a) a start-up process which comprises filling the mixing device and the reactor with hexafluoroisopropanol.

6. The process of claim 1 wherein hydrogen is added in step (a) in an amount and at a rate to produce of solution of hexafluoroacetone and hexafluoroisopropanol saturated with hydrogen.

7. The process of claim 1 wherein the mixing device is an autoclave.

8. The process of claim 1 wherein hydrogen is fed to maintain a pressure of 300-2000 psig (2.17-13.9 MPa).

9. The process of claim 8 wherein hydrogen is fed to maintain a pressure of 400-1500 psig (2.86-10.4 MPa).

10. The process of claim 9 wherein hydrogen is fed to maintain a pressure of 600-1000 psig (4.24-7.00 MPa).

11. The process of claim 1 wherein hydrogen bubbles form during step (a) and further comprising disengaging the bubbles prior to step (b).

12. The process of claim 1 wherein concentration of hexafluoroisopropanol in the feed stream is from 85 to 98 mole % and the concentration of hexafluoroacetone is from 2 to 15 mole %.

13. The process of claim 12 wherein concentration of hexafluoroisopropanol in the feed stream is from 93 to 97 mole % and the concentration of hexafluoroacetone is from 3 to 7 mole %.

14. The process of claim 1 wherein the contacting step is performed at a temperature to provide a feed stream having a temperature of 75-160° C. and wherein the hydrogenating step (b) is performed at a catalyst bed temperature of 75-160° C.

15. The process of claim 2 wherein the reactor has an upflow configuration.

16. The process of claim 2 wherein the reactor has a downflow configuration.

17. The process of claim 3 further comprising cooling the portion of the product stream prior to recirculating the portion of the stream to step (a).

18. The process of claim 1 wherein the catalyst comprises a catalytic metal and a support.

19. The process of claim 1 wherein the catalyst comprises a catalytic metal and the catalytic metal is selected from the group consisting of chromium, molybdenum, tungsten, iron, cobalt, nickel, copper, ruthenium, rhodium, palladium, osmium, iridium and platinum.

20. The process of claim 19 wherein the catalytic metal is nickel.

21. The process of claim 18 wherein the support is selected from the group consisting of alumina, silica, zirconia, activated charcoal, calcium silicate, graphite, and kieselguhr.

22. The process of claim 18 wherein the catalytic metal content of the catalyst is 45 to 60 wt %, based on the total weight of the catalyst.

23. The process of claim 18 wherein the catalytic metal content of the catalyst is 0.5 to 10 wt %, based on the total weight of the catalyst.

24. The process of claim 1 wherein the recovering step (c) comprises cooling the product stream; reducing pressure of the product stream; and separating the cooled, de-pressurized stream to a gas/liquid separator in which hydrogen is separated from HFIP.

* * * * *